US007094552B2

(12) United States Patent  
Thomasi et al.

(10) Patent No.: US 7,094,552 B2  
(45) Date of Patent: Aug. 22, 2006

(54) DIAGNOSTIC TEST KITS

(75) Inventors: Jean-Paul Thomasi, Brussels (BE); Michel Gersdorff, Brussels (BE); Guy Rousseau, Brussels (BE)

(73) Assignee: Universite Catholique de Louvain, Louvain-la-Neuve (BE)

( * ) Notice: Subject to any disclaimer, the term of this patent is extended or adjusted under 35 U.S.C. 154(b) by 244 days.

(21) Appl. No.: 10/272,601

(22) Filed: Oct. 16, 2002

(65) Prior Publication Data

US 2003/0082171 A1 May 1, 2003

Related U.S. Application Data

(60) Division of application No. 09/611,908, filed on Jul. 7, 2000, now abandoned, which is a continuation of application No. 09/125,754, filed as application No. PCT/EP97/01003 on Feb. 28, 1997, now abandoned.

(30) Foreign Application Priority Data

Mar. 4, 1996 (GB) .................................. 9604595.0  
Mar. 12, 1996 (GB) .................................. 9605229.5

(51) Int. Cl.  
G01N 33/53 (2006.01)  
G01N 33/559 (2006.01)  
G01N 33/564 (2006.01)

(52) U.S. Cl. ...................... 435/7.1; 435/810; 530/350; 424/184.1

(58) Field of Classification Search ............. 424/184.1; 435/810  
See application file for complete search history.

(56) References Cited

U.S. PATENT DOCUMENTS 5,576,423 A * 11/1996 Aversa et al. .......... 530/388.75  
5,925,736 A 7/1999 Neff et al.

OTHER PUBLICATIONS

Stryer et al, in Biochemistry, Third edition, W H Freeman Company, New York, pp. 31-33, 1998.*  
Kuby et al, 1994, Immunology, Second edition, pp. 86-96.*  
Colman et al, 1994, A structural view of immune recognition by antibodies, pp. 33-36.*  
Jelloun-Dellagi et al, Ann Neurol 32(5): 700-2, Nov. 1992.*  
Bauerfeind et al, Z Rheumatol 53(2): 66-71, abstract only, Mar.-Apr. 1994.*  
Ming Y. Cao et al., "Myelin Protein PO as a Potential Autoantigen in Autoimmune Inner Ear Disease" Faseb Journal, (Dec. 1996), vol. 9, pp. 1635-1640.  
Rudick R.A. et al., "Treatment of Multiple Sclerosis" (1992) Chapter 15: Experimental Approaches to Specific Imunotherapy in Multiple Sclerosis (David A. Hafler et al.), pp. 301-307.  
Greg Lemke et al., "Isolation and analysis of the Gene Encoding Peripheral Myelin Protein Zero" Neuron, (Mar. 1988), vol. 1, p. 73-83.

Czerkinsky et al., "Cholera Toxin B Subunit: An efficient transmucosal carrier—delivery system for induction of peripheral immunological tolerance," Proc. Natl. Acad. Sci., USA (1994) vol. 91, pp. 10795-10799.  
Cao et al., Molec. and Cell. Biochem., (1994) vol. 146, pp. 157-163.  
Ishaque et al., Can. J. Biochem., (1980) vol. 58, p. 913-921.  
Bernard et al., Immunology, (1981) 43; 447-457.  
Ngo et al., The Protein Folding Problem and Tertiary Structure Prediction. K. Merz, Jr. and S. Le Grand, Editors, Birkhauser Boston, 1994, pp. 492-495.  
Swiss Prot_39 Accession No. P27573, 1992.  
Gerin et al., Abstract, Sequence of a putative glucose 6-phosphate translocase, mutated in glycogen storage disease type Ib, FEBS Lett., Feb. 26, 1999, pp. 449-450, vol. 445, No. 2-3.  
Joliat et al., Abstract, Antibodies against a 30 kilodalton cochlear protein and type II and IX collagens in the serum of patients with inner ear diseases, Ann Otol Rhinol Laryngol, Dec. 1992, pp. 1000-1006, vol. 101, No. 12.  
Lai et al., Two forms of IB236/myelin-associated glycoprotein, a cell adhesion molecule for postnatal neural development, are produced by alternative splicing, Proc. Natl. Acad. Sci, Jun. 1987, pp. 4337-4341, vol. 84, USA.  
Milner et al., Abstract, P0 myelin protein produces experimental allergic neuritis in Lewis rats, Journal of the Neurological Sciences, Jul. 1987, pp. 275-285, vol. 79, Issue 3.  
Sedzik et al., Abstract, Purification of P0 myelin glycoprotein by a Cu2+-immobilized metal affinity chromatography, Neurochem. Res., Jun. 1999, pp. 723-732, vol. 24, No. 6.  
Shelly et al., Isolation of the gene for murine glucose-6-phosphatase, the enzyme deficient in glycogen storage disease type 1A, J. Biol. Chem., 1993, pp. 21482-21485, vol. 268, Issue 29.  
Cao et al., Abstract, The localization and specificity of guinea pig inner ear antigenic epitopes, J. Laryngol Otol., Jan. 1995, pp. 19-23, vol. 109, No. 1.  
Harris et al., Abstract, Inner ear autoantibodies in patients with rapidly progressive sensorineural hearing loss, Laryngoscope, May 1990, pp. 516-524, vol. 100, No. 5.  
Veldman et al., Abstract, Diagnostic and therapeutic dilemmas in rapidly progressive sensorineural hearing loss and sudden deafness. A reappraisal of immune reactivity in inner ear disorders, Acta Otolaryngol. May 1993, pp. 303-306, vol. 113, No. 3.  
Barna et al., Abstract, Autoimmune inner ear disease—a real entity? Clin Lab Med, Sep. 1997, pp. 581-594, vol. 17, No. 3.

(Continued)

Primary Examiner—Christina Chan  
Assistant Examiner—Phuong N Huynh  
(74) Attorney, Agent, or Firm—TraskBritt

(57) ABSTRACT

The invention provides a method for the treatment of prophylaxis of autoimmune inner ear disease, in particular, deafness caused by autoimmune inner ear disease, which comprises administering to a host in need thereof a vaccine comprising peripheral myelin protein zero. The invention further provides diagnostic methods and kits derived from the protein.

4 Claims, No Drawings

OTHER PUBLICATIONS

Hayasaka et al., Abstract, Structure and chromosomal localization of the gene encoding the human myelin protein zero (MPZ), Genomics, Sep. 1993, pp. 755-758, vol. 17, No. 3.

Hayasaka et al., Abstract, Isolation and sequence determination of cDNA encoding the major structural protein of human peripheral myelin, Biochem. Biophys. Res. Commun., Oct. 31, 1991, pp. 515-518, vol. 180, No. 2.

Yamanobe et al., Abstract, Extraction of inner ear antigens for studies in inner ear autoimmunity, Ann. Otol. Rhinol. Laryngol., Jan. 1993, pp. 22-27, vol. 102.

Soliman, AM, Abstract, Autoantibodies in inner ear disease, Acta Otolaryngol., Jul. 1997, pp. 501-504, vol. 117, No. 4.

Findlay, J.B.C., Purification of membrane proteins, Protein purification applications, a practical approach, Chapter 4, 1990; pp. 59-82, IRL press, UK, eds. Harris & Angal.

Moscicki et al., Detection of Serum Antibody to Inner Ear Antigens in Patients with Idiopathic Progressive Bilateral Sensorineural Hearing Loss (IPBSNHL), J. Allergy Clin Immunol. 1990, pp. 145, vol. 85.

* cited by examiner

SEQUENCE LISTING

<160> NUMBER OF SEQ ID NOS: 11

<210> SEQ ID NO 1
<211> LENGTH: 248
<212> TYPE: PRT
<213> ORGANISM: Guinea Pig

<400> SEQUENCE: 1

```
Met Ala Pro Gly Ala Pro Ser Ser Pro Ser Pro Ile Leu Ala Ala
 1               5                  10                  15

Leu Leu Phe Ser Ser Leu Val Leu Ser Pro Ala Leu Ala Ile Val Val
                20                  25                  30

Tyr Thr Asp Arg Glu Ile Tyr Gly Ala Val Gly Ser Gln Val Thr Leu
             35                  40                  45

His Cys Ser Phe Trp Ser Glu Trp Val Ser Asp Ile Ser Phe
 50                  55                  60

Thr Trp Arg Tyr Gln Pro Glu Gly Gly Arg Asp Ala Ile Ser Ile Phe
 65                  70                  75                  80

His Tyr Ala Lys Gly Gln Pro Tyr Ile Asp Glu Val Gly Ala Phe Lys
                 85                  90                  95

Glu Arg Ile Gln Trp Val Gly Asp Pro Arg Trp Lys Asp Gly Ser Thr
                100                 105                 110

Val Ile His Asn Leu Asp Tyr Ser Asp Asn Gly Thr Phe Thr Cys Val
                115                 120                 125

Asp Lys Asn Pro Pro Asp Ile Val Gly Lys Thr Ser Gln Val Thr Leu
130                 135                 140

Tyr Val Phe Glu Lys Val Pro Thr Arg Tyr Gly Val Val Leu Gly Ala
145                 150                 155                 160

Val Ile Gly Gly Ile Leu Gly Val Val Leu Leu Leu Leu Leu Leu Phe
                165                 170                 175

Tyr Leu Ile Arg Tyr Cys Trp Leu Arg Arg Gln Ala Ala Leu Gln Arg
                180                 185                 190

Arg Leu Ser Ala Met Glu Lys Gly Arg Phe His Lys Ser Ser Lys Asp
                195                 200                 205

Ser Ser Lys Arg Gly Arg Gln Thr Pro Val Leu Tyr Ala Met Leu Asp
                210                 215                 220

His Ser Arg Ser Thr Lys Ala Ala Ser Glu Lys Lys Ser Lys Gly Leu
225                 230                 235                 240

Gly Glu Ser Arg Lys Asp Lys Lys
                245

<210> SEQ ID NO 2
<211> LENGTH: 6
<212> TYPE: PRT
<213> ORGANISM: Guinea Pig

<400> SEQUENCE: 2

Gly Leu Gly Glu Ser Arg
 1               5

<210> SEQ ID NO 3
<211> LENGTH: 6
<212> TYPE: PRT
<213> ORGANISM: Guinea Pig

<400> SEQUENCE: 3

Gln Ala Ala Leu Gln Arg
 1               5

<210> SEQ ID NO 4
<211> LENGTH: 7
<212> TYPE: PRT
<213> ORGANISM: Guinea Pig

<400> SEQUENCE: 4
```

```
Ile Val Val Tyr Thr Asp Arg
 1               5

<210> SEQ ID NO 5
<211> LENGTH: 8
<212> TYPE: PRT
<213> ORGANISM: Guinea Pig

<400> SEQUENCE: 5

Ile Gln Trp Val Gly Asp Pro Arg
 1               5

<210> SEQ ID NO 6
<211> LENGTH: 14
<212> TYPE: PRT
<213> ORGANISM: Guinea Pig

<400> SEQUENCE: 6

Gln Thr Thr Val Leu Tyr Ala Met Leu Asp His Tyr Ser Arg
 1               5                  10

<210> SEQ ID NO 7
<211> LENGTH: 14
<212> TYPE: PRT
<213> ORGANISM: Guinea Pig

<400> SEQUENCE: 7

Gly Gln Pro Tyr Ile Asp Glu Val Gly Ala Phe Lys Glu Arg
 1               5                  10

<210> SEQ ID NO 8
<211> LENGTH: 12
<212> TYPE: PRT
<213> ORGANISM: Guinea Pig

<400> SEQUENCE: 8

Gly Gln Pro Tyr Ile Asp Glu Val Gly Ala Phe Lys
 1               5                  10

<210> SEQ ID NO 9
<211> LENGTH: 17
<212> TYPE: PRT
<213> ORGANISM: Guinea Pig

<400> SEQUENCE: 9

Tyr Gln Pro Glu Gly Gly Arg Asp Ala Ile Ser Ile Phe His Tyr Ala
 1               5                  10                  15

Lys

<210> SEQ ID NO 10
<211> LENGTH: 13
<212> TYPE: PRT
<213> ORGANISM: Guinea Pig

<400> SEQUENCE: 10

Gln Thr Pro Val Leu Tyr Ala Met Leu Asp His Ser Arg
 1               5                  10

<210> SEQ ID NO 11
<211> LENGTH: 23
<212> TYPE: PRT
<213> ORGANISM: Guinea Pig

<400> SEQUENCE: 11
```

-continued

```
Ile Val Val Tyr Thr Asp Arg Glu Val His Gly Ala Val Gly Ser Gln
1               5                   10                  15

Val Thr Leu His Cys Ser Phe
            20
```

DIAGNOSTIC TEST KITS

CROSS-REFERENCE TO RELATED APPLICATIONS

This application is a divisional of Ser. No. 09/611,908, filed Jul. 7, 2000, now abandoned, which is a continuation of U.S. application Ser. No. 09/125,754, filed Sep. 29, 1998, abandoned, which is a 371 of International Application Serial No. PCT/EP97/01003, filed Feb. 28, 1997, published as PCT International Publication Number WO 97/32598 on Sep. 12, 1997, the contents of which are incorporated by this reference.

TECHNICAL FIELD

This invention relates to novel vaccine and pharmaceutical formulations and to their manufacture and use in the treatment of deafness. In particular, the invention relates to the use of the protein known as major peripheral myelin protein zero (abbreviated to MPP, Pzero or Po) in a vaccine. The invention further relates to the use of the protein in diagnostic methods and to a kit for use in carrying out such methods.

BACKGROUND

There is a high incidence of inner ear diseases such as progressive sensorineural hearing loss, sudden deafness, otosclerosis and Meniere's disease. The etiology of these inner ear diseases remains unclear or unknown. However, evidence now suggests that certain inner ear diseases, including those above, appear to be of autoimmune origin. In patients with inner ear disease, several attempts have been made to identify specific antigens with which circulating antibodies and active lymphocytes react. Antibodies against type II collagen and heat shock protein p70 have been described in patients suffering from idiopathic inner ear disease (e.g. Yoo et al., Science 1982, 217, 1153–1155).

It is known that the 30,000-$M_r$ (30 kDa) protein present in guinea pig inner ear is recognized by autoantibodies in sera from patients with inner ear disease. The 30,000-$M_r$ inner ear antigen has been partially purified by chromatography (M Y Cao et al., Mol Cell Biochem. 1995, 146, 157–163). This inner ear antigen has now been sequenced, and partial internal sequences and N-terminal sequence (in total 84 amino acids) of this protein have been obtained. It has been found that the 30 000-$M_r$ inner ear protein is the major myelin protein zero (MPP, Pzero, Po). The complete sequence of the bovine, rat, mouse, chick, and human proteins has been determined. Each contains 229 amino acids and a signal peptide of 29 amino acids. Po is highly conserved between species and the interspecific replacement rate of Po between human and guinea pig is very low.

BRIEF SUMMARY OF THE INVENTION

As a consequence of these findings, it is expected that the Po protein may be an important autoantigen in the pathogenesis of autoimmune disease, and that the Po protein may, therefore, be useful for the diagnosis, treatment or prevention of autoimmune inner ear disease.

Therefore, in a first aspect, the present invention provides the use of major peripheral myelin protein zero as an autoantigen, and the use of major peripheral myelin protein zero in a vaccine. Suitably, the vaccines of the invention are used for the treatment of autoimmune inner ear diseases, in particular, deafness caused by autoimmune inner ear disease. Preferably, the peripheral myelin protein zero has the sequence shown in SEQ ID NO:1 or is a derivative or fragment thereof having substantially the same immunological activity.

Preferably, the major peripheral myelin protein zero is in substantially pure form, that is to say, major peripheral myelin protein zero substantially free of other proteins or materials. By "substantially pure" is meant preferably greater than 60% pure, more preferably over 75% pure, advantageously over 90% pure, for example 95–100% pure.

In a further aspect, the invention provides a method for the treatment or prophylaxis of autoimmune inner ear disease, in particular, deafness caused by autoimmune inner ear disease, which comprises administering to a host in need thereof a vaccine comprising peripheral myelin protein zero.

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each dose will comprise about 1–1000 mg of protein, preferably about 1–200 mg. An optimal amount for a particular vaccine can be ascertained by standard studies involving observation of antibody titres and other responses in subjects.

In another aspect, the invention provides for diagnostic use of major peripheral myelin protein zero. In particular, the invention provides an immunoassay for detecting antibodies directed against a Po antigen comprising contacting a biological sample, for example, blood or serum, with a polypetptide under conditions that allow for the formation of an antibody-antigen complex and detecting antibody-antigen complexes comprising said polypeptide, wherein said polypeptide comprises an antigenic determinant of the major peripheral myelin protein zero.

DETAILED DESCRIPTION OF THE INVENTION

A number of protocols for carrying out immunoassays are known, which may, for example, be based upon competition, or direct reaction, or sandwich assays. Protocols may use solid supports or may be by immunoprecipitation. Immunoassays generally involve the use of labeled antibody or polypeptide. The labels may be, for example, fluorescent, chemiluminescent, radioactive, or dye molecules. A particular aspect of the invention provides a polypeptide comprising an antigenic determinant of the major peripheral myelin protein zero, attached to said substrate.

Diagnostic kits for use in the present invention can be constructed by packaging the necessary materials, including said polypeptide, optionally on a solid support, in a container with a set of instructions.

The major peripheral myelin protein zero can be obtained and purified using standard techniques well known to those skilled in the art.

The following experimental details illustrate the invention.

EXPERIMENTAL

Sera and tissue extracts. Sera from patients with inner ear disease were the same as previously described. All gave a strong signal with the 30,000-$M_r$ inner ear antigen in immunoblots. Sera from normal individuals were taken as negative controls. Inner ear tissues were obtained from 200 g Hartley guinea pigs of both sexes. The inner ear tissues were separated into two different tissue pools during the microdissection. The "total tissue pool" included the organ of Corti, the basilar membrane, the spiral ligament, the stria vascularis, the spiral ganglion and the acoustic nerve in the modiolus, as well as the vestibular organ. The "modiolus pool" consisted of the acoustic nerve and the spiral ganglion. Each of these pools was homogenized by ultrasonication at 20 kHz in 10⁻ volumes of Tris-HCl buffer. The homogenate was centrifuged (8000 g×10 min at 4° C.) and the supernatant was kept as the water soluble fraction. The pellets were resuspended in 10 volumes of buffer containing 10 mM Tris-HCl, 1 mM EDTA, 2.5% (w/v) SDS and 5% (v/v) 2-mercaptoethanol, pH 7.4, and supplemented with the following protease inhibitors: 10 mg/ml antipain, 2 mg/ml pepstatin, 40 mg/ml phenylmethylsulphonyl fluoride, 10 mg/ml chymostatin and 10 mM N-ethylmaleimide. The suspension was centrifuged (8000 g×10 min at 4° C.) and the supernatant was filtered through a 0.22 μm filter to yield the SDS-soluble fraction. The water-soluble and SDS-soluble fractions were boiled for 5 min and the protein concentration was adjusted with the respective buffers to 1 mg/ml. The resulting preparations were stored frozen at −20° C. for further analysis. Extracts from the sciatic nerve were likewise prepared from guinea pigs for comparison with extracts from acoustic nerve. The sciatic nerve was dissected from the guinea pigs and extracted as described above.

Two-dimensional gel electrophoresis. Two dimensional gel electrophoresis was carried out with modifications in a mini-gel system (BioRad). Protein extracts were diluted 10 times with first-dimension sample buffer (9.5 M urea, 2% (w/v) NP-40, 5% 2-Mercaptoethanol, 1.6% (v/v) Ampholine™ pH 5–7, 0.4% (v/v) Ampholine™ pH 3.5–10 to reduce the concentration of SDS to 0.25%. Protein extracts were loaded onto individual gels. Proteins were visualized with 0.25% Coomassie brilliant blue R-250 or transferred to nitrocellulose membrane for immunoblotting.

Electrophoresis. Protein extracts were prepared for one dimensional SDS-PAGE by adding an equal volume of sample buffer, containing 10% (v/v/) glycerol. A calibration protein sample (Pharmacia LKB, Uppsala) for molecular weight determination was also prepared. The protein extracts were separated by mini-SDS-PAGE in 0.5 mm-think gels containing 15% (w/v) acrylamide according to the method of Laemmli, Nature 1970, 227, 680–685, or by ultra-thin precast 10% to 15% SDS polyacrylamide gradient gels (43×50×0.45 mm) (Pharmacia) using an automated electrophoresis apparatus (Phast System, Pharmacia). Protein bands were visualized by 0.25% (w/v) Coomassie brilliant blue R-250 staining or transferred to polyvinylidine difluoride (PVDF) membranes—(Millipore Corp., Bedford, Mass.) for immunoblotting.

Immunoblotting. Following two-dimensional gel electrophoresis or SDS-PAGE, the separated proteins were transferred onto PVDF membranes as described by Towbin et al., Proc. Nat. Acad. Sci. USA 1979, 76, 4350–4356, using a mini Trans-Blot™ cell (BioRad). The efficiency of the transfer was checked by staining the gels following electroelution. The PVDF membrane was dried. The lane of the calibration protein was cut from the transferred membrane and stained with Amido Black (0.1% Amido Black B-10, 45% Methanol and 10% Acetic acid solution) and destained with 25% Methanol and 7% Acetic acid solution. The remaining PVDF membrane was used for the immunoblot.

The blots were washed with Tris-Buffer Saline (TBS, 20 mM Tris-HCl, 500 mM NaCl, pH 7.5) for 10 min, and incubated for 2 hrs at room temperature with 5% (v/v) non-fat dry milk in TTBS (TBS and 0.5% Tween-20, pH 7.5), followed by 3h of incubation with 1/50 dilution of the test sera in 5% milk at room temperature. The blots were washed twice in TTBS, and incubated again for 2 hrs with a 1/600 dilution of an alkaline phosphatase-conjugated second antibody (rabbit anti-human IgA, IgG, IgM (DAKO, Denmark) in TBS. Finally, the blots were washed twice in TTBS and once in TBS, and developed with a freshly prepared solution of alkaline phosphatase-conjugate substrate (Bio-Rad, Calif.).

N-terminal amino acid sequence analysis. This was made following separation in an agarose 15% (v/v) acrylamide SDS gel treated to remove free radicals. The protein was transferred to a PVDF membrane (Problott™, Applied Biosystems) in 10 mM Caps, pH 11, 10% (v/v) methanol and an electrophoretic cell (Trans-Blot™, BioRad) at 5 V overnight. Following transfer, the membrane was rinsed in transfer buffer (25 mM Tris, 192 mM glycine, 20% (v/v) methanol, pH 8.3), stained for 2 min in 0.25% (w/v) Coomassie brilliant blue R-250, 40% (v/v) methanol and destained in acetic acid/methanol/$H_2O$ (1:5:4, by vol). The membrane was then washed in distilled water 5 times and air dried. The part of the membrane corresponding to the 30,000-$M_r$ protein bands was used for the N-terminal sequencing by automated Edman degradation on an Applied Biosystems automatic sequencer (models 477A) equipped with a 120 A phenylthiohydantoin-amino-acid analyzer.

Electroelution of the 30,000-$M_r$ inner ear protein for microsequencing and MALDI-TOF mass spectrometry. An agarose-based concentration gel was cast as described. Bands corresponding to the 30,000-$M_r$ protein and containing an estimated 50 μg of protein were excised from SDS-PAGE gels and concentrated into an agarose gel as described by Rider et al., Eur J Biochem., 1995, 230, 258–265. The protein spot was excised from the agarose gel and melted in 0.1 M Tris-HCl pH 8.6, 5% (v/v) acetonitrile, 0.2% (w/v) octylglucoside. The protein was digested with trypsin (0.2 μg) at 30° C. overnight. The mixture was frozen at −80° C. for 2h, thawed and centrifuged to remove the precipitated agarose for narrow-bore reverse-phase HPLC. Peak fractions in the HPLC elution profile were monitored by the absorbance at 214 mm, collected manually in Eppendorf tubes and microsequenced as described above. Aliquots of peaks from the HPLC (1 μl) were spotted onto the target strip of the MALDI-TOF mass spectrometer (Finnigan Mat Lasermat 2000), mixed with 1 μl of matrix which was a saturated solution of α-cyano-4-hydroxycinnamic acid in 0.1% (v/v) trifluoroacetic acid/acetronitrile (2:1, v/v) and allowed to air dry. Peptide masses were measured with 20–30 laser shots with the machine calibrated on substance P (mass=1347.6).

Other methods and reagents. Protein was measured by the method of Bradford. Computer searching for homologous sequences in the SwissProt database was made using the BLAST program. Peptide mass fingerprinting was made in the MOWSE database—see Pappin et al., Curr. Biol., 1993, 3, 327–332.

Results

Solubilization and purification of the 30,000-$M_r$ protein in SDS-polyacrylamide gels. Inner ear extracts were electrophoresed in ultra-thin precast 10–15% SDS gradient gels using the Phast system and stained with Coomassie blue. Lane 1—sample extracted in Tris buffer without SDS in acoustic nerve and spiral ganglion. Lane 2—total inner ear proteins extracted in SDS sample buffer. Lane 3—sample extracted from the acoustic nerve and spiral ganglion in SDS sample buffer. Several bands including one of 30,000-$M_r$ were seen with the "total tissue pool" from inner ear prepared in the presence of SDS. The 30,000-$M_r$ band was the only band seen with SDS extracts of the "modiolus pool." By contrast, no band was seen when the "modiolus pool" was prepared in the absence of SDS, or in the presence of non-ionic detergents such as NP-40 of Triton X-100. This suggested that the protein is hydrophobic and might be associated in vivo with cell membranes. After immunoblotting, the 30,000-$M_r$ band was recognized by sera from the patients. In two-dimensional gels, the 30,000-$M_r$ protein extracted from the "modiolus pool" was detected as a diffuse spot by Coomassie Bue staining or by immunoblotting. The same data were obtained with the "total tissue pool." Immunoblotting was carried out as follows: The extract from the acoustic nerve and spiral ganglion was subjected to isoelectric focusing (IEF),then SDS-polyacrylamide gel electrophoresis. The proteins on the two-dimensional gel were transferred onto a nitrocellulose membrane. The blot was subsequently probed with a serum from a patient with inner ear disease. One spot, corresponding to the 30,000-$M_r$ inner ear protein was identified by comparison with protein standards.

Identification of the 30,000-$M_r$ by protein microsequencing and peptide mass fingerprinting. The 30,000-$M_r$ band from the "modiolus pool" was electroeluted onto a PVDF membrane for N-terminal sequencing by classical automated Edman degradation. Twenty-three amino acids were obtained (Table 1). A protein data bank search showed that these correspond to residues 30 to 52 of the major peripheral myelin protein (MMP, Po). There was an identity score of 98% with human Po, 96% with rat Po, 95% with mouse Po, and 93% with bovine Po. Residues 1–29 of Po correspond to the single peptide. The identity of the 30,000-$M_r$ protein as protein Po was confirmed by peptide mass fingerprinting. Protein bands corresponding to the 30,000-$M_r$ protein were taken from a one-dimensional gel of the "total tissue pool," electroeluted and concentrated in our agarose gel-concentration system for digestion with trypsin Rider et al., Eur J Biochem., 1995, 230, 258–265. The narrowbore reverse-phase HPLC profile of the tryptic digest of the protein was obtained as follows: The 30,000-$M_r$ inner ear protein was separated in a 0.5 mm thick one dimensional gel, passed through an agarose concentration gel, melted and digested with trypsin. Peaks eluting from the narrow-bore reverse-phase HPLC were detected at 214 nm. The individual peaks numbered 1–26 were collected by hand in Eppendorf tubes for further analysis. By taking aliquots from peaks in the HPLC for MALDI-TOF mass spectrometry, we were able to obtain some masses of tryptic peptides (Table 1). When these masses were fed into the MOWSE peptide mass fingerprinting database, mouse myelin Po protein precursor (mass=27621 Da) was first hit with a score of 0.778. The score was not 1.0 because two masses could not be matched despite the fact neither of them correspond to trypsin autodigestion fragments. One of these (peak 14) was found to correspond to the N-terminal tryptic heptapeptide which has a theoretical mass of 865 Da (Table 1). This peptide had no match in the database because of the presence of the single peptide. The peptide corresponding to the other mass (1549.9 Da=peak 18, Table 1) was taken for microsequencing. Its sequence corresponds to residues 215–227 of the mouse Po protein precursor with a mutation of Pro-217 to Thr. The discrepancy between the measured mass of 1549.9 and the calculated mass of 1534.8 for the sequence in peak 18 could be explained by the presence of 3-methylhistidine. Microsequencing of peak 26 gave a sequence identical to that present in the mouse Po protein precursor (residues 215–227), in which Pro-217 was conserved. This suggests that the 30,000-$M_r$ band contains two forms of the Po protein, one of which has a Pro-217 to Thr mutation. Such a mutation, which could correspond to allelic variation, would not affect the overall charge of the protein and, therefore, the two forms would not be resolved by isoelectric focusing in two-dimensional gels. The position of the peptides described in Table 1 with respect to the sequence of the mouse Po protein precursor is shown in SEQ ID NO:1. Amino acid sequence of mouse Po precursor protein showing positions of the peptides were analyzed by HPLC/MALDI-TOF mass spectrometry or Edman sequencing. The emboldened numbers correspond to the positions of the tryptic peptides (Table 1). The Edman sequences of guinea pig 30,000-$M_r$ antigen are shown in italics.

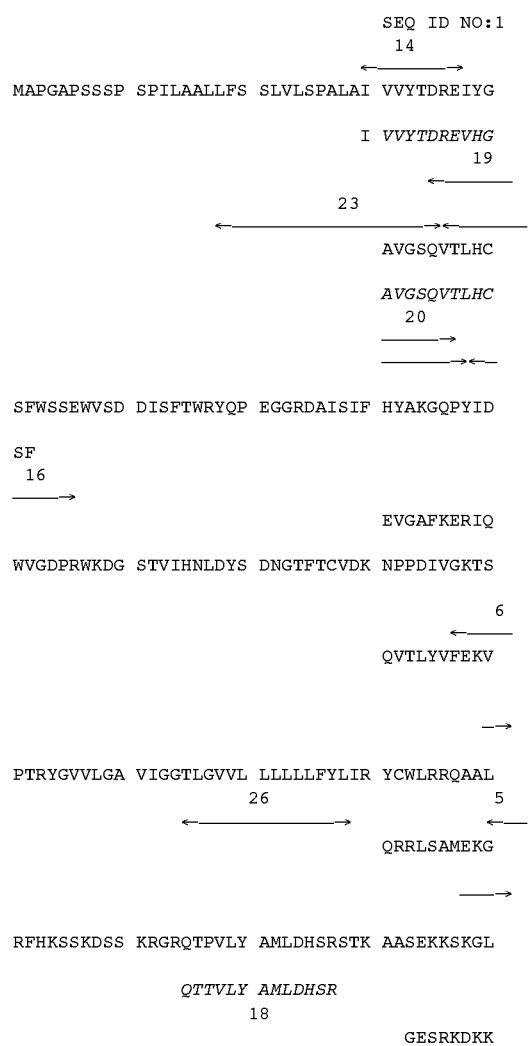

Additional Experimental Data. SDS-Page patterns of the inner ear and sciatic nerve extracts. The extracts from the sciatic nerve and the acoustic nerve in the modiolus were co-migrated on SDS-PAGE gel, and stained with Coomassie blue. Lane 1—the extract from the sciatic nerve; Lane 2—the extract from the acoustic nerve and spiral ganglion; a single spot appears in each lane at about 30 kDa.

TABLE 1

Analysis of the 30 000 $M_r$ inner ear antigen by Edman degradation and MALDI-TOF mass spectrometry.

| HPLC peak No. | Mol Mass (Da) Measured | Mol Mass (Da) Theoretical | Sequence | | Position in mouse Po precursor |
|---|---|---|---|---|---|
| 5 | 618.5 | 617.7 | GLGESR | (SEQ ID NO:2) | 239–244 |
| 6 | 686.3 | 685.8 | QAALQR | (SEQ ID NO:3) | 187–192 |
| 14* | 865.4 | — | IVVYTDR | (SEQ ID NO:4) | 30–36 |
| 16 | 970.8 | 970.1 | IQWVGDPR | (SEQ ID NO:5) | 99–106 |
| 18* | 1549.9 | — | QTTVLYAMLD(H)(Y)SR | (SEQ ID NO:6) | 215–227 |
| 19+ | 1608.5 | 1608.8 | GQPYIDEVGAFKER | (SEQ ID NO:7) | 85–98 |
| 20 | 1325.3 | 1323.5 | GQPYIDEVGAFK | (SEQ ID NO:8) | 85–96 |
| 23+ | 1952.8 | 1952.2 | YQPEGGRDAISIFHYAK | (SEQ ID NO:9) | 68–84 |
| 26 | 1531.5 | 1530.8 | QTPVLYAMLDHSR | (SEQ ID NO:10) | 215–227 |
| N-Terminus | — | — | IVVYTDREVHGAVGSQVTLHCSF | (SEQ ID NO:11) | 30–52 |

The underlined sequences were obtained by Edman degradation. Measured masses correspond to masses of tryptic peptides in peaks from the HPLC determined by MALDI-TOF mass spectrometry. Their sequences were assigned after feeding all of the measured masses into the MOWSE peptide database. + indicates masses derived from partial cleavages. * indicates "no match" masses. Theoretical masses were calculated from the mouse Po precursor sequence using the computer program "Peptidesort" in the GCG package.

Generation of EASNHL in Guinea Pigs

An experimental model of autoimmune sensorineural hearing loss was established by immunizing Hartley guinea pigs with an emulsion of 400 μg/ml of PO-protein antigen in complete Freund's adjuvant. The animals were boosted at three and eight weeks with 50 μg of PO-protein antigen in incomplete Freund's adjuvant. Between 1 and 4 weeks later, serum was taken for Western blot analysis and the animals were killed. The hearing of these animals was tested electrophysiologically by measuring brainstem auditory-evoked potential (BAEP). At various times up to 72 days post immunization, BAEP was recorded on a Nicolet CA-1000 system. In the BAEP study, all of the peak and interpeak latencies were prolonged significantly. The minimal hearing thresholds were elevated slightly. Furthermore, tests for antibodies to PO antigen were performed with their serum. An immunoblot analysis (Western Blot) showed that an antibody from the hearing loss animals specifically reacted with the 30,000 Dalton molecular weight antigen identified as the PO-protein.

Oral Immunization with Po Antigens in the Guinea Pig Model

In a second step, we developed immuno-intervention to ameliorate the disease processes leading into deafness by inducing oral tolerance. We used the protocol recently reported by Czerkinsky et al. A single oral administration of 500 μg of PO-antigen coupled to the B subunit of cholera toxin (CTB) can markedly suppress systemic immune responses in naive and in systemically immune Guinea pigs. Both early (2–4 hr) and late (24–48 hr) delayed-type hypersensitivity reactivities were strongly suppressed after feeding a single dose of CTB-conjugated-PO. Serum antibody responses were also decreased, although moderately, after oral administration of CTB-conjugated PO. This strategy of vaccination, based on oral administration of small amounts of PO conjugated to CTB, may find applications for preventing or abrogating hearing loss in humans.

Radioimmunoassay for Detecting Anti-Po Antibodies in Sera from Affected Individuals Solid phase radioimmunoassay to detect antibodies to Po antigens can be developed based upon Tsu and Herzenberg (1980). Microtitre plates are coated with purified polypeptides containing Po epitopes. The coated plates are incubated with either human serum samples from patients with inner ear disease or appropriate controls. During incubation, antibody, if present, is immunologically bound to the solid phase antigen. After removal of the unbound material and washing of the microtitre plates, complexes of human antibody-Po antigen are detected by incubation with $^{125}$I-labeled sheep anti-human immunoglobulin. Unbound labeled antibody is removed by aspiration and the plates are washed. The radioactivity in individual wells is determined: the amount of bound human anti-Po antibody is proportional to the radioactivity in the well.

The invention claimed is:

1. A diagnostic test kit for diagnosing autoimmune inner ear disease, said diagnostic kit comprising:
 a polypeptide comprising SEQ ID NO: 1, attached to a solid substrate.

2. The diagnostic test kit of claim 1 wherein the solid substrate is a membrane for carrying out an immunoblot.

3. A diagnostic kit for diagnosing autoimmune inner ear disease, said diagnostic kit comprising:
 means for contacting a biological sample with a polypeptide comprising SEQ ID NO: 1 under conditions that allow for the formation of an antibody-antigen complex between the polypeptide and any antibodies presented in the biological sample, and
 means for detecting antibody-antigen complexes comprising said polypeptide, wherein formation of the antibody-antigen complex is indicative of the autoimmune inner ear disease of the subject.

4. A test for diagnosing autoimmune inner ear disease, said test comprising:
 a polypeptide comprising an antigenic determinant of the major peripheral myelin protein zero, attached to a solid substrate, and in contact with a tissue sample comprising antibodies, wherein said tissue sample is from a subject suffering from autoimmune inner ear diseases, wherein said polypeptide comprises SEQ ID NO: 1.

* * * * *

UNITED STATES PATENT AND TRADEMARK OFFICE
CERTIFICATE OF CORRECTION

PATENT NO. : 7,094,552 B2  Page 1 of 1
APPLICATION NO. : 10/272601
DATED : August 22, 2006
INVENTOR(S) : Jean-Paul Tomasi, Michel Gersdorff and Guy Rousseau It is certified that error appears in the above-identified patent and that said Letters Patent is hereby corrected as shown below:

CLAIM 4, COLUMN 14, LINES 20,21 change "autoimmune inner ear diseases," to --autoimmune inner ear disease,--

Signed and Sealed this

Twenty-third Day of December, 2008

JON W. DUDAS
*Director of the United States Patent and Trademark Office*